United States Patent [19]

Wiest

[11] 3,982,533

[45] Sept. 28, 1976

[54] INSUFFLATION APPARATUS

[75] Inventor: Peter P. Wiest, Berlin, Germany

[73] Assignee: F. M. Wiest KG, Germany

[22] Filed: Aug. 27, 1975

[21] Appl. No.: 608,163

[30] Foreign Application Priority Data

Mar. 14, 1975 Germany.................... 7508556[U]

[52] U.S. Cl............................... 128/184; 137/557; 128/218 N; 128/2 R
[51] Int. Cl.²...................................... A61M 13/00
[58] Field of Search............ 128/184, 218 N, 145.5, 128/145.8, 2.05 D, 2 R; 137/557

[56] References Cited
UNITED STATES PATENTS

| | | | |
|---|---|---|---|
| 2,001,638 | 5/1935 | Tornsjo | 128/184 |
| 3,794,026 | 2/1974 | Jacobs | 128/145.8 |
| 3,870,072 | 3/1975 | Lindemann | 128/184 |
| 3,885,590 | 5/1975 | Ford et al. | 128/184 |

Primary Examiner—Robert W. Michell
Assistant Examiner—Henry J. Recla
Attorney, Agent, or Firm—McGlew and Tuttle

[57] ABSTRACT

The apparatus, used for introducing limited quantities of carbon dioxide into the human body for operational purposes, particularly laparoscopy, includes a control device for delivering the carbon dioxide, a connecting nipple on the control device for connecting a flexible tubing to a Veress needle introducable into the body and a pressure gauge for indicating the pressure present in the body cavity. A second connection nipple is provided on the control device and connected by a nipple to the pressure gauge. The second connection nipple is connected by a further flexible tubing either to a dual Veress needle or to a second single Veress needle, so that the pressure gauge is directly connected with the body cavity rather than through the operative Veress needle.

7 Claims, 5 Drawing Figures

ID_982,533

INSUFFLATION APPARATUS

FIELD AND BACKGROUND OF THE INVENTION

The present invention relates to an insufflation apparatus for introducing limited quantities of carbon dioxide into the human body for operational purposes, particularly for laparoscopy, comprising a control device for delivering the carbon dioxide, a connecting nipple for connecting a flexible tubing to a Veress needle which is introductible into the body cavity, and a pressure gauge for indicating the pressure present in the body cavity.

In a known insufflation apparatus of this kind, it is not possible to measure the pressure, building up in the body cavity, accurately. This is due to the fact that, during the insufflation, a backpressure builds up at the Veress needle, which is comprised in the indication of the pressure gauge and thus leads to a false reading of the actual pressure in the body cavity. The backpressure may amount to the order of magnitude of 30 to 40 mm Hg. The backpressure, of course, depends on the adjusted delivery pressure of the apparatus. Since it is important to the operator to know the actual internal pressure at the beginning of the laparoscopy, a co-indication of the backpressure leads to a misinterpretation of the position of the Veress needlepoint.

SUMMARY OF THE INVENTION

The present invention is directed to an insufflation apparatus of the mentioned kind permitting an accurate measuring of the intra-abdominal pressure, i.e. the pressure in the interior of the body cavity, already at the start of the laparoscopy.

For this purpose, in accordance with the invention, the pressure gauge is connected, through a pipe, directly to a second connecting nipple which is adapted to be connected to a flexible tubing through which a direct connection to the body cavity can be established.

Thereby, any erroneous indication caused by the backpressure at the Veress needle is eliminated because the backpressure does not enter into the measuring. As is well known, backpressure is produced at any necking and simultaneous increase of the velocity, and thus, in the case of the Veress needle, at the transition from the tubing connection to the hollow needle proper. By providing a second connecting nipple which is directly connected, through the pipe and thus in a pressure-fluid conducting manner, to the indicating gauge, a direct measuring of the intra-abdominal pressure through this second connecting nipple is made possible.

This second connecting nipple may be connected to a double-way or dual Veress needle or also to a second Veress needle. In either case, the measuring error due to the backpressure is eliminated.

Advantageously, in one embodiment of the invention, the second connecting nipple is provided on the front panel of the insufflation apparatus, close to the first connecting nipple to which it is connectable by means of a flexible tubing. In another embodiment, the pressure gauge and the second connecting nipple are provided in the front panel of a separate pressure meter, and the second connecting nipple is connectable to the first connecting nipple of the insufflation apparatus through a flexible tubing. This interconnectability of the connecting nipples has the advantage that, prior to the start of the insufflation, the adjusted delivery values to be furnished by the insufflation apparatus can be checked on the pressure gauge of the insufflation apparatus or of the separate pressure meter.

This checking is made on the provided pressure gauge. For this purpose, a step switch is provided on the front panel of the insufflation apparatus, and has a plurality of operational positions adapted to adjust the apparatus, in these positions, to a plurality of insufflation degrees. Upon bridging the two connecting nipples by the flexible tubing, the pressures are readable on the pressure gauge.

An object of the invention is to provide an improved insufflation apparatus for introducing limited quantities of carbon dioxide into the human body.

Another object of the invention is to provide such an insufflation apparatus which permits an accurate measuring of the intra-abdominal pressure at the start of a laparoscopy.

A further object of the invention is to provide such an improved insufflation apparatus in which erroneous indications, caused by backpressure at a Veress needle, are eliminated.

For an understanding of the principles of the invention, reference is made to the following description of typical embodiments thereof as illustrated in the accompanying drawings.

DESCRIPTION OF THE PREFERRED EMBODIMENTS

Figure 1:
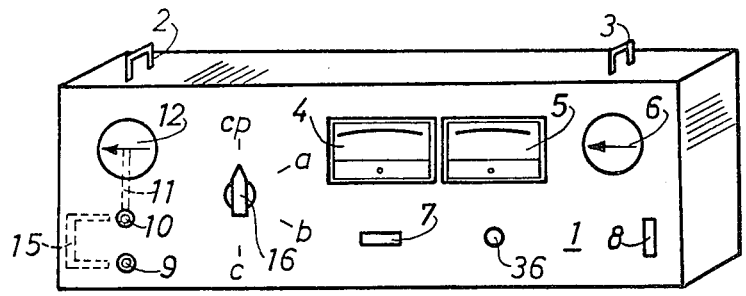
FIG. 1 is a diagrammatical perspective view of the front panel of a first embodiment of the insufflation apparatus.

In the first embodiment according to FIG. 1, the housing of the insufflation apparatus comprises a front panel 1 and two handles 2 and 3. On the front panel, two indicators 4 and 5 are provided, one for the electronic $CO_2$ measurement and the other for the filling of the body cavity with $CO_2$. A pressure gauge 6 on the front panel indicates the $CO_2$ supply reserve in the gas bottle. Also mounted on the front panel is a switch 7 for admitting or interrupting the insufflation gas stream and a switch 8 for switching the power supply on or off. The connecting nipple 9 is the gas outlet of the apparatus to be connected, according to FIGS. 2 and 3, by means of a flexible tubing 13a, to the Veress needle.

In accordance with the invention, a second connecting nipple 10 is provided on the front panel 1. Through a pipe 11, this connecting nipple 10 is directly connected to a pressure gauge 12. Through the connectable flexible tubing 13, second connecting nipple 10 establishes a direct communication with the body cavity 14 as shown in FIGS. 2 and 3.

The two connecting nipples 9 and 10 are interconnectable by means of a flexible tube 15 which makes it possible to check the permanently adjusted delivery pressures of the insufflation apparatus on pressure gauge 12. Pressure gauge 12 is only a checking instrument for the operational positions of a step switch 16 provided on front panel 1. In the position CP of switch 16, the filling pressure is maintained constant during the laparoscopy and any gas loss is compensated. The positions a, b, c correspond to any operational pressure with different filling quantities.

Figure 2:
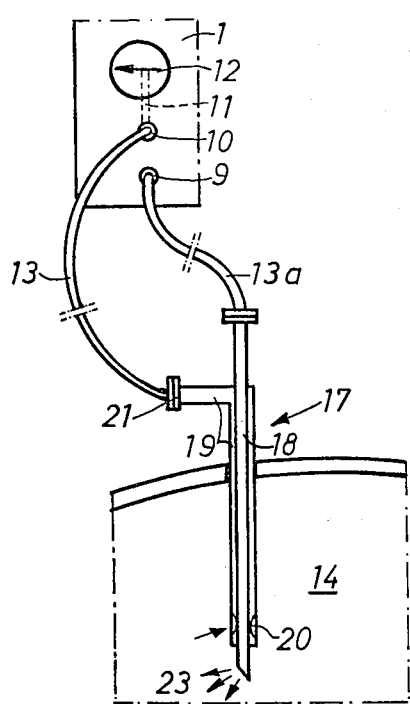
FIG. 2 shows the connection of the two connecting nipples of the insufflation apparatus of FIG. 1 to a double-way or dual Veress needle.

FIG. 2 shows a double-way or dual Veress needle 17. The needle comprises an inner needle 18 and a hollow jacket 19. Close to the needle point, jacket 19 is provided with a plurality of oblong apertures 20 distributed over the circumference. Hollow jacket 19 is closed at its outer end adjacent the needle point and provided, on its end remote from the needle point, with an outlet nipple 21 to be connected to a flexible tubing 13 which, in its turn, is connected to the second connecting nipple 10 and, through pipe 11, to pressure gauge 12.

Figure 3:
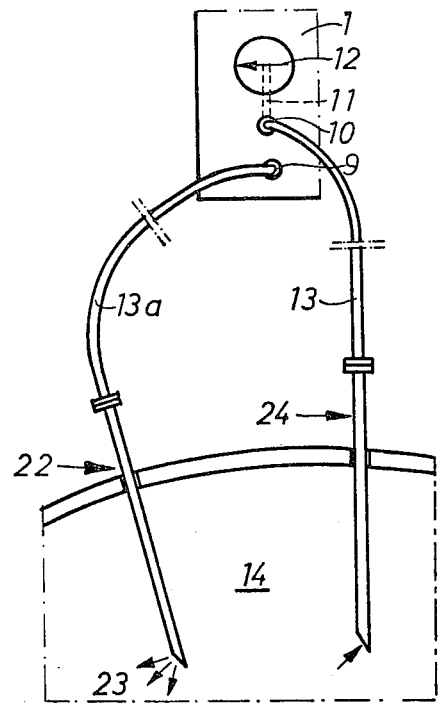
FIG. 3 shows the connection of the connecting nipples of the insufflation apparatus of FIG. 1 to two respective Veress needles.

FIG. 3 illustrates the possibility of insufflating with the aid of two Veress needles, in which case the gas is insufflated into the body cavity 14 through a needle 22, in the direction of arrow 23, and the pressure present in the body cavity is transmitted through a Veress needle 24, the flexible tubing 13, the second connecting nipple 10, and the pipe 11, for being measured by pressure gauge 12.

Figure 4:
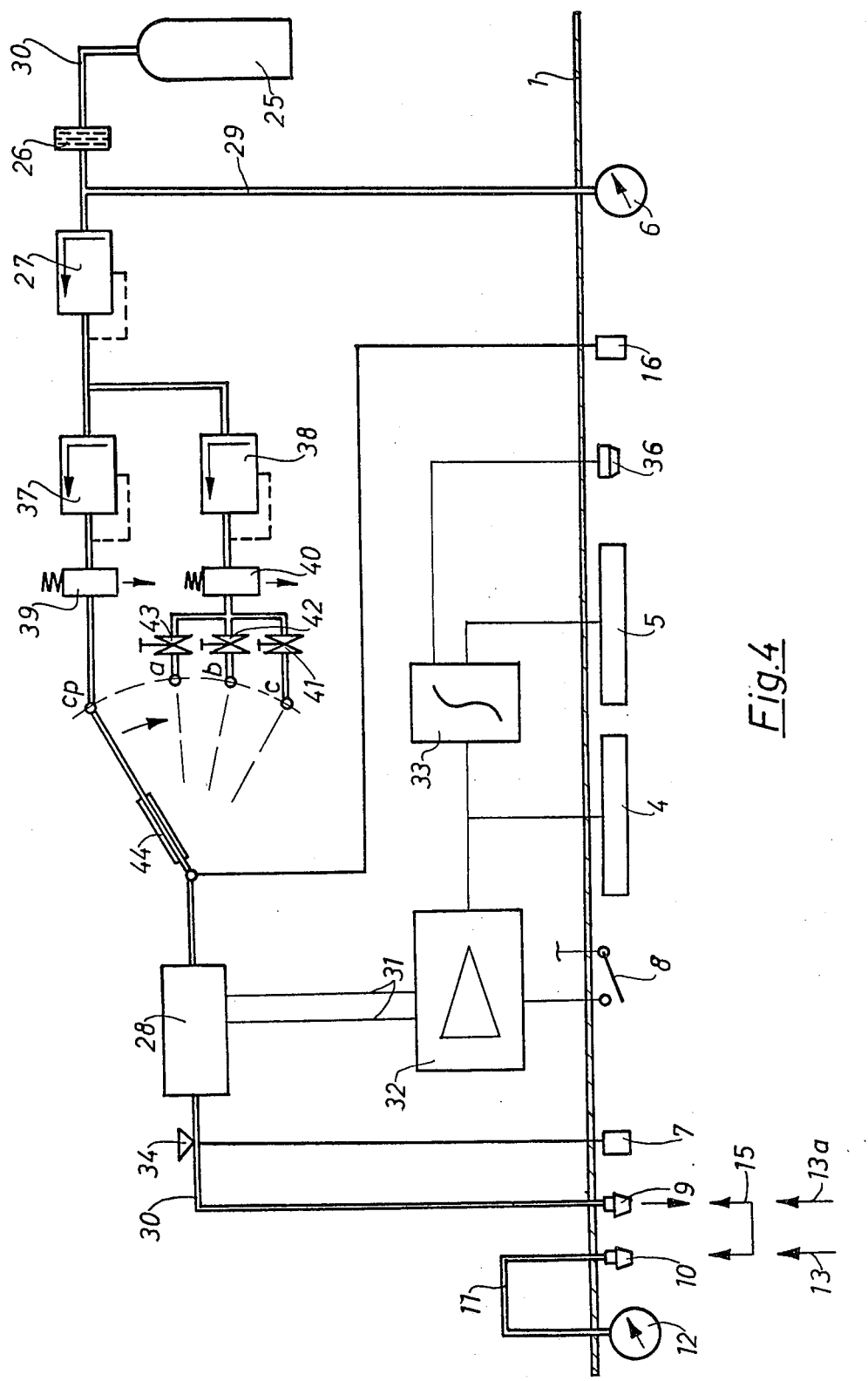
FIG. 4 is a schematic diagram of the insufflation apparatus of FIG. 1.

The control device shown in FIG. 4, of the insufflation apparatus according to the first embodiment illustrated in FIG. 1, comprises a gas bottle 25 wherefrom $CO_2$ gas is supplied, through a filter 26 and a first pressure reducer 27, to a gas flow controlling device 28. Upstream of pressure reducer 27, a line 29 is branched off the main line 30, and leads to pressure gauge 6 which indicates the pressure reserve within the gas bottle 25. In a manner not shown in detail, measuring impulses are taken off the gas flow control device 28 and are delivered, in the form of electric pulses, through lines 31 and electric components comprising an amplifier 32 and an integrator 33, to the indicators 4 and 5. Indicator 4 indicates the gas flow per minute and indicator 5 indicates the total volume of supplied gas. Integrator 33 is connected to a key 36 for the zero setting of indicator 5. Main line 30 leads to connecting nipple 9 for connection to the Veress needle through flexible tubing 13a. A valve 34, actuable by switch 7, is provided between connecting nipple 9 and the gas flow control device 28, for admitting or interrupting the insufflation gas stream.

The device for selecting the different operational positions CP, a, b and c, actuable by step switch 16, is mounted in the main line 30, between the first pressure reducer 27 and the gas flow control device 28. This selecting device comprises two micro pressure reducers 37, 38 mounted in parallel and followed by excess pressure safety valves 39, 40, and precision orifices 41, 42 and 43 which are mounted after the excess pressure safety valve 40. The outlets of the parallel lines of main line 30 determine the different operational positions CP, a, b, c, which can be adjusted through switch 16 and by means of a selector switch 44.

Components parts 4, 5, 6, 7, 8, 9, 16 and 36 are mounted on front panel 1. The same applies to the second connecting nipple 10 which is connectable to flexible tubing 13 and to pressure gauge 12 which is permanently connected, through pipe 11, to second connecting nipple 10. Second connecting nipple 10 can be connected, through flexible tube 15, to the first connecting nipple 9.

Figure 5:
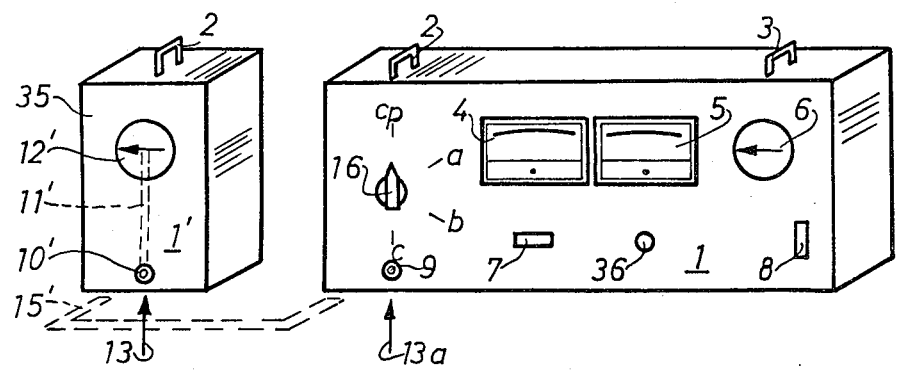
FIG. 5 is a view, similar to FIG. 1, of a second embodiment of the insufflation apparatus comprising a separate pressure meter.

The second embodiment shown in FIG. 5 differs from the first embodiment as shown in FIGS. 1 to 4 in that the pressure gauge 12' and the second connecting nipple 10' are mounted on the front panel 1' of a separate pressure meter 35. Such a pressure meter may advantageously be used with conventional insufflation apparatus which are not yet provided with a second connecting nipple for direct measuring of the actual pressure in the body cavity 14. For checking measurements, second connecting nipple 10' of separate pressure meter 35 and first connecting nipple 9 on the front panel 1 of the insufflation apparatus may be connected to each other by a flexible tubing 15'.

While specific embodiments of the invention have been shown and described in detail to illustrate the application of the principles of the invention, it will be understood that the invention may be embodied otherwise without departing from such principles.

What is claimed is:

1. In an insufflation apparatus, including means for introducing limited quantities of carbon dioxide into the human body for operational purposes, particularly for laparoscopy, and further including a control device for delivering the carbon dioxide having a first outlet connection nipple, a Veress needle, a first flexible tubing connected at one end to said Veress needle introduceable into a body cavity and at the opposite end to said first nipple, and a pressure gauge for indicating the pressure in the body cavity, the improvement comprising, in combination, a second connection nipple on said control device; a pipe connecting said pressure gauge to said second connection needle; a second flexible tubing connected at one end to said second connection nipple, means connected to the opposite end of said second tubing introduceable into said body cavity and adapted to be spaced from the tip of said Veress needle for detecting pressure within said body cavity, and means selectively operable to interconnect said first and second nipples.

2. In an insufflation apparatus, the improvement claimed in claim 1, in which said Veress needle is a double-way Veress needle having an outer jacket with lateral openings spaced from the tip of the Veress needle; said second flexible tubing connecting said second connection nipple to said outer jacket.

3. In an insufflation apparatus, the improvement claimed in claim 1, in which said last-named means comprises a second Veress needle connected by said further flexible tubing to said second connection nipple.

4. In an insufflation apparatus, the improvement claimed in claim 1, in which said control device has a front panel mounting said first-mentioned connection nipple; said second connection nipple being mounted on said front panel close to said first-mentioned connection nipple; and said means selectively operable to interconnect the two connection nipples includes a flexible tubing.

5. In an insufflation apparatus, the improvement claimed in claim 1, including a separate pressure meter having a front panel; said second connection nipple being mounted on said front panel of said separate pressure meter; a pressure gauge mounted on said front panel of said separate pressure meter and connected directly to said second connection nipple; and said means selectively operable to interconnect said second connection nipple and said first-mentioned connection nipple includes a flexible tubing.

6. In an insufflation apparatus, the improvement claimed in claim 5, including a step switch means mounted on said front panel and having a plurality of operational pressure positions in each of which said first-mentioned connection needle is subjected to a respective different pressure of the carbon dioxide; whereby the respective pressures are readable on said pressure gauge responsive to bridging of said connection nipples by said selectively operable means.

7. In an insufflation apparatus, the improvement claimed in claim 1, including a step switch means mounted on said front panel and having a plurality of operational pressure positions in each of which said first-mentioned connection needle is subjected to a respective different pressure of the carbon dioxide; whereby the respective pressures are readable on said pressure gauge responsive to bridging of said connection nipples by said selectively operable means.

* * * * *